(12) United States Patent
Nissilä et al.

(10) Patent No.: US 6,600,942 B2
(45) Date of Patent: *Jul. 29, 2003

(54) SCREEN

(75) Inventors: Seppo Nissilä, Kempele (FI); Hannu Kinnunen, Oulu (FI); Pekka Rytky, Oulu (FI); Jean-Pierre Baumann, Fleurier (FI)

(73) Assignee: Polar Electro Oy, Kempele (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/978,961

(22) Filed: Oct. 17, 2001

(65) Prior Publication Data

US 2002/0026112 A1 Feb. 28, 2002

Related U.S. Application Data

(63) Continuation of application No. 09/335,663, filed on Jun. 18, 1999, now Pat. No. 6,327,486.

(30) Foreign Application Priority Data

Jun. 22, 1998 (FI) .................................................. 981436

(51) Int. Cl.⁷ ............................................. A61B 5/0408
(52) U.S. Cl. ...................... 600/372; 600/382; 600/390; 600/393; 600/509; 128/903
(58) Field of Search ................ 600/372, 382, 600/390, 393, 509; 128/903

(56) References Cited

U.S. PATENT DOCUMENTS

| | | | | |
|---|---|---|---|---|
| 442,315 A | * | 12/1890 | Segawa ...................... 400/324 |
| 3,500,823 A | * | 3/1970 | Richardson et al. ......... 600/372 |
| 3,620,208 A | * | 11/1971 | Higley et al. ................ 600/395 |
| 3,706,308 A | * | 12/1972 | John et al. ................... 600/483 |
| 3,868,947 A | * | 3/1975 | Holsinger ..................... 600/382 |
| 3,880,146 A | * | 4/1975 | Everett et al. ............... 600/523 |
| 4,122,843 A | * | 10/1978 | Zdrojkowski ................ 600/382 |
| 4,709,702 A | * | 12/1987 | Sherwin ...................... 600/383 |
| 4,763,660 A | * | 8/1988 | Kroll et al. .................... 439/77 |
| 5,140,992 A | * | 8/1992 | Zuckerwar et al. .......... 600/528 |
| 5,417,221 A | * | 5/1995 | Sickler ......................... 128/901 |
| 5,483,967 A | * | 1/1996 | Ohtake ........................ 600/509 |
| 5,491,474 A | * | 2/1996 | Suni et al. ................... 128/903 |
| 5,645,073 A | * | 7/1997 | Kadefors et al. ............ 600/546 |
| 6,327,486 B1 | * | 12/2001 | Nissila et al. ................ 600/372 |

FOREIGN PATENT DOCUMENTS

| | | | |
|---|---|---|---|
| DE | 2610337 | * | 9/1977 |
| WO | WO 91/09565 | * | 7/1991 |

* cited by examiner

*Primary Examiner*—Lee Cohen
(74) *Attorney, Agent, or Firm*—Hoffmann & Baron, LLP

(57) ABSTRACT

The invention relates to a screen (300), which is particularly intended for a functional unit measuring heart rate from a user's chest. Electrodes (304) of the functional unit and preferably also an electric circuit (306) are protected against extracorporeal interference by the screen (300), which closely follows the electrode (304) or a supporting structure (40, 50, 60, 70) at least at the electrode (104, 204, 304, 402, 502, 602, 702).

4 Claims, 8 Drawing Sheets

SCREEN

This application is a continuation of application Ser. No. 09/335,663, filed on Jun. 18, 1999., now U.S. Pat. No. 6,327,486.

FIELD OF THE INVENTION

The invention relates to a screen which is particularly intended for a non-invasive functional unit measuring the function of at least one organ through skin contact, the functional unit comprising a supporting structure, an electrical circuit for operation, and electrodes for the skin contact, the electrodes being operatively coupled to the electrical circuit and mechanically attached to the supporting structure.

BACKGROUND OF THE INVENTION

Vital functions can be measured telemetrically using a non-invasive measuring device. An example of such a measuring device is, for example, a system which measures human heart rate and usually comprises as functional units a transmitter unit, a receiver unit and a data transfer unit. The transmitter unit refers to a transmitter unit equipped with electrodes and worn on the human body, particularly on the chest, the transmitter unit usually being implemented in the form of a transmitter belt attached around the body. The receiver unit refers for instance to a watch-like receiver unit which is worn on the wrist, the receiver unit having a telemetric or wired coupling with the transmitter unit. The data transfer unit transfers data received in the receiver unit to a computer, for example. The computer can also control the transmitter unit and the receiver unit via the data transfer unit.

Heart rate measurement is based on monitoring the function of the heart. When the heart contracts, it generates a series of electric impulses that can be measured in the body. The measurement and analysis of this signal is called electrocardiography (ECG). The signal itself is called an ECG signal. Different phases of the heart cycle can be discerned in the ECG signal. These are called P, Q, R, S, T and U waves.

The transmitter part located next to the body suffers from electromagnetic interference, and particularly from problems caused by static electricity. A typical problem situation occurs when a user exercises with a shirt on. When the user moves, the shirt moves, flapping against the user's body and the transmitter unit. Synthetic fiber textiles in particular that are poor at conducting electricity attract electric charges specifically in dry weather, at least before the user starts sweating. In terms of electrical engineering, a great amount of charge at random amplitude and at random frequency then moves in the vicinity of the transmitter unit. Such a random movement of a great amount of charge is capacitively coupled to the transmitter unit, interfering with its operation.

BRIEF DESCRIPTION OF THE INVENTION

An object of the invention is thus to provide a screen so as to solve the above problems caused by static electricity. This is achieved with a screen described in the introduction, the screen being characterized by being arranged to closely follow the electrode or the supporting structure at least at the electrode.

A plurality of advantages can be achieved by the screen of the invention. The screen prevents disturbance from being connected to the functional unit; hence, the operation of the functional unit becomes more reliable.

BRIEF DESCRIPTION OF THE DRAWINGS

The invention is now described in closer detail in connection with the preferred embodiments with reference to the accompanying drawings, in which.

DETAILED DESCRIPTION OF THE INVENTION

The inventive solution is particularly suited for protecting a transmitter unit of a heart-rate-measurement system against electric interference, but a similar solution may also benefit other kind of devices.

Figure 1A:
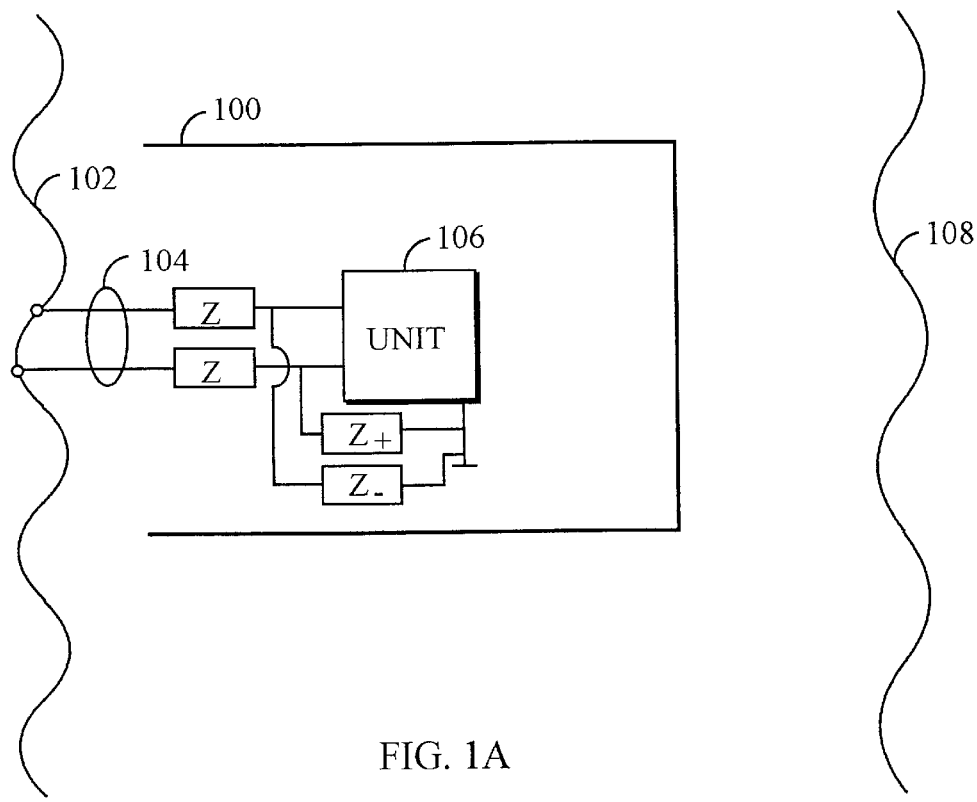
FIG. 1A shows an electric coupling of a screen when the screen is not connected to skin.

Examine first an inventive solution by means of FIG. 1A showing a screen 100, skin 102, electrodes 104, an electrical circuit 106 of a functional unit and a source 108 of disturbance. The functional unit is for example a transmitter unit of a system measuring the function of an organ of a user, the transmitter unit comprising the two electrodes 104. The electrodes 104 have an electric and usually also galvanic contact with the skin 102. The interference source 108 is for example a shirt or another piece of clothing the user is wearing. When the shirt moves on the user, the shirt becomes electrically charged. The charge tends to cause interference to the operation of the electrical circuit 106 of the transmitter unit through capacitive and/or resistive coupling. In the inventive solution, such generation of interference can be prevented by using the screen 100 between the interference generator 108 and both the electrodes 104 and the electrical circuit 106. Used as a protection for the electrodes 104 and the electrical circuit 106, the screen 100, which is preferably an electrically conductive material layer, reduces all types of electromagnetic interference being connected to the electrical circuit 106. The electrodes 104 can be coupled to a signal earth via impedances $Z_+$ and $Z_-$ which can be of different magnitude. Impedance $Z_-$ of the two impedances can have a very low impedance.

Figure 1B:
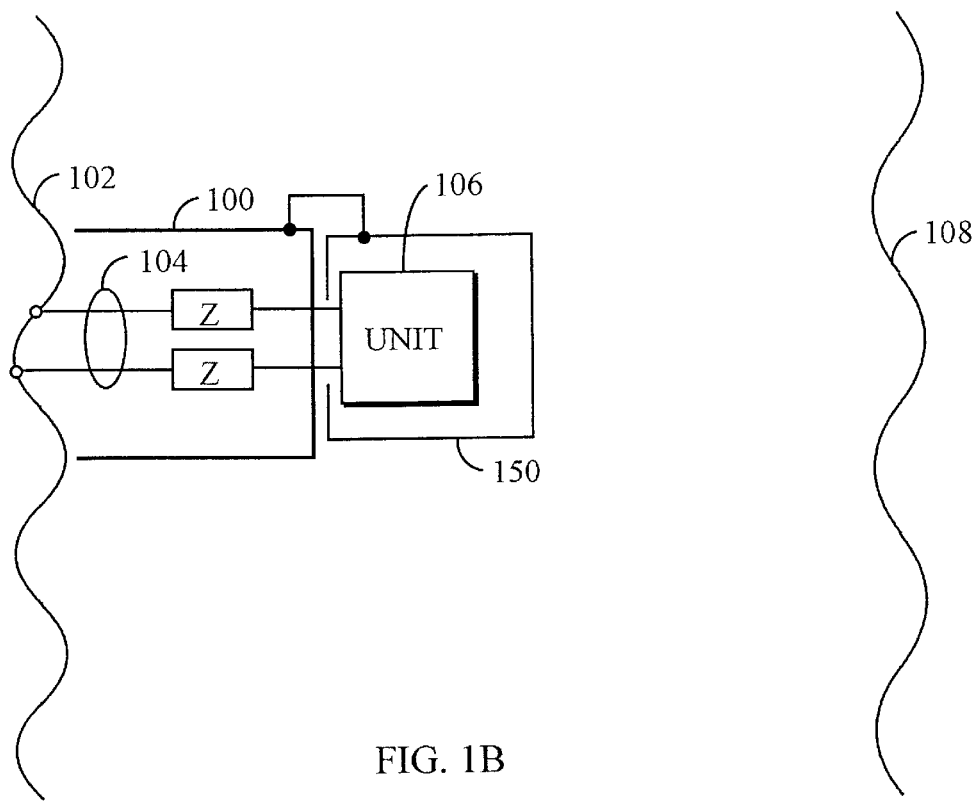
FIG. 1B shows the screen's electric coupling, which protects electrodes.

FIG. 1B shows a solution similar to the one in FIG. 1A, with the exception that here the screen 100 only protects the electrodes 104. Furthermore, in the inventive solution the electrical circuit 106 is protected with a unique screen 150, which is preferably electrically coupled to the screen 100.

Figure 2:
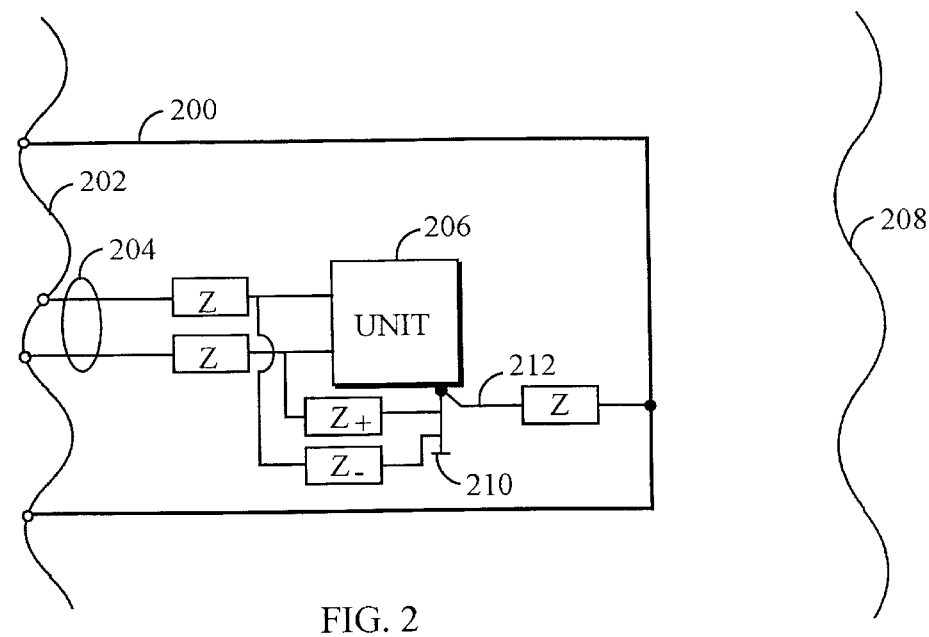
FIG. 2 shows the electric coupling of the screen when the screen is connected to skin.

FIG. 2 shows an inventive solution wherein a screen 200 is electrically coupled to skin 202. FIG. 2 also encompasses electrodes 204, a generator 208 of interference, and a signal earth 210 of an electrical circuit 206 of a transmitter unit. The screen 200 can preferably be electrically coupled also with a signal earth 210 by a conductor 212, which can have impedance component Z; such a coupling is not, however, necessary for the invention. The electrodes 204 can also be coupled to the signal earth via impedances $Z_+$ and $Z_-$, which can be of different magnitude. Impedance $Z_-$ of the two impedances can have a very low impedance. The signal earth 210 protects the operation of the circuit 206 against interference.

Figure 3:
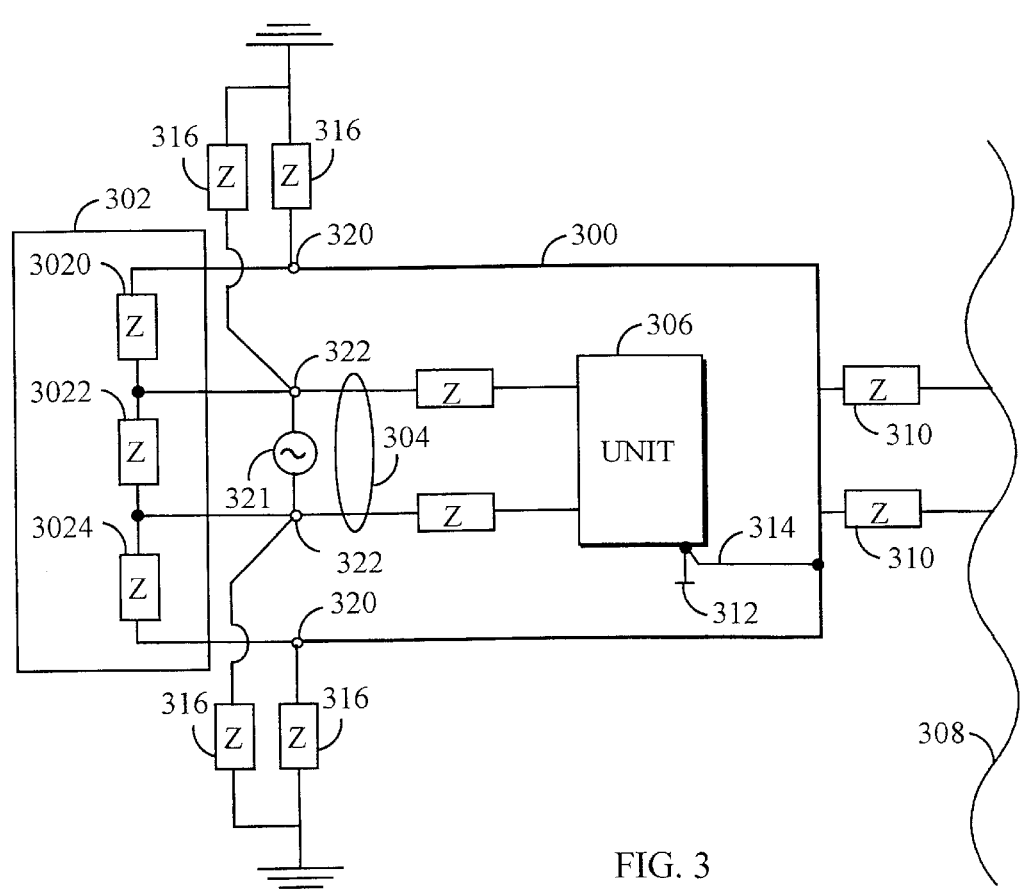
FIG. 3 shows an example of an equivalent circuit.

FIG. 3 shows an equivalent circuit of the inventive solution. FIG. 3 encompasses a screen 300, skin 302, electrodes 304, an electrical circuit 306 of a transmitter unit, a generator 308 of interference, interference impedances 310, a signal earth 312, a conductor 314 from the signal earth 312 to the screen 300, and an impedance 316. Instead of only comprising the conductor 314, the coupling can further be provided with an impedance, as in FIG. 2. The equivalent circuit of the skin 302 comprises impedances 3020, 3022, 3024. Between the measuring electrodes 304 there is provided the impedance 3022, over which voltage impulses are generated for example when heart rate is being measured. Heart rate typically provides the electrodes with an approximately 2 mV potential difference, which is presented by a signal source 321. Correspondingly, the impedances 3020 and 3024 are located between the electrodes 304 and the skin contact of the screen 302. This clearly shows that it may not be desirable to provide the skin contacts 320 of the screen 302 too near electrode contacts 322, since a resistive coupling would then exist along the screen 300 between the contacts 322 of the electrodes 304, the resistive coupling lowering the voltage caused for example by heartbeat to be measured. The impedances 310, which typically are capacitances, represent the capacitive coupling caused by the shirt 308 generating the interference to the screen 300. The screen 300 and the contacts 322 of the electrodes 304 are coupled to earth via impedances 316. On the other hand, it is generally known that the resistance level is high and the coupling typically capacitive; hence, coupling is poor.

Figure 4A:
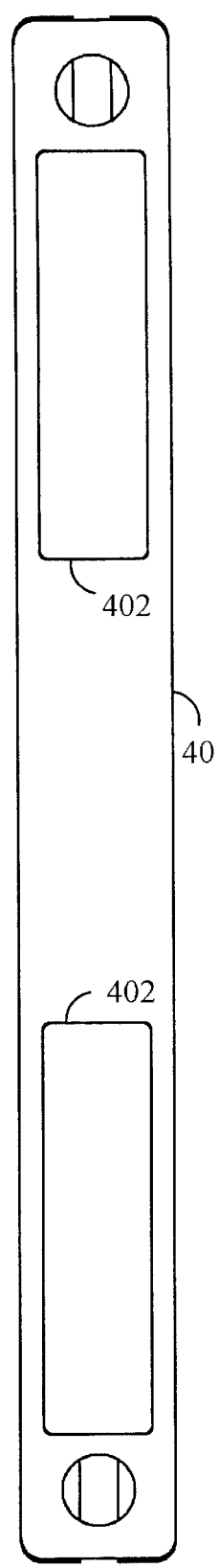
FIGS. 4A and 4B show a transmitter unit when the screen is on the outer surface of the transmitter unit.
Figure 4B:
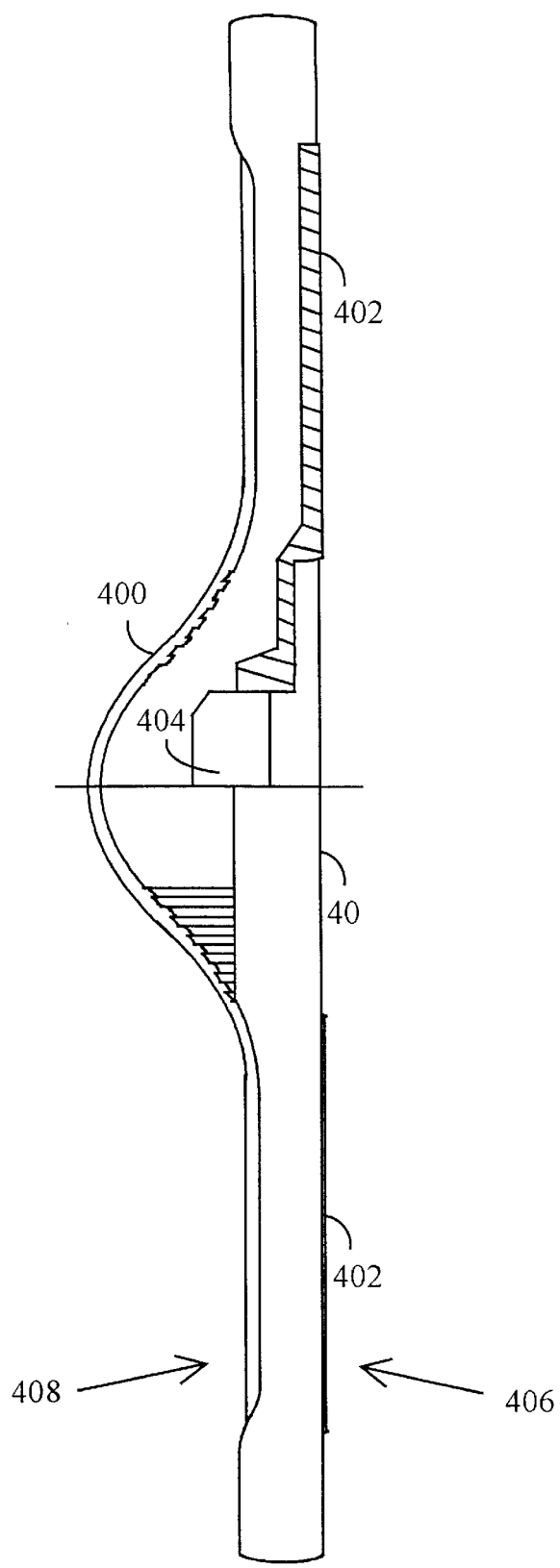

FIGS. 4A and 4B show a transmitter unit, which is coated with a screen. An electrical circuit 404 of the transmitter unit is preferably encased in a belt part to be attached around the chest. A belt-like encasement structure, which serves as a supporting structure 40, is usually made of flexible, plastic-like material, which is not electrically conductive. On the belt-like transmitter unit's surface next to skin, which can be called a surface 406 with skin contact, there are provided electrodes 402. The rest of the transmitter's surface is here defined as a surface 408 without skin contact. Hence, a screen 400 is preferably situated on the plastic encasement structure, being substantially located at the surface 408 without skin contact.

Figure 5A:
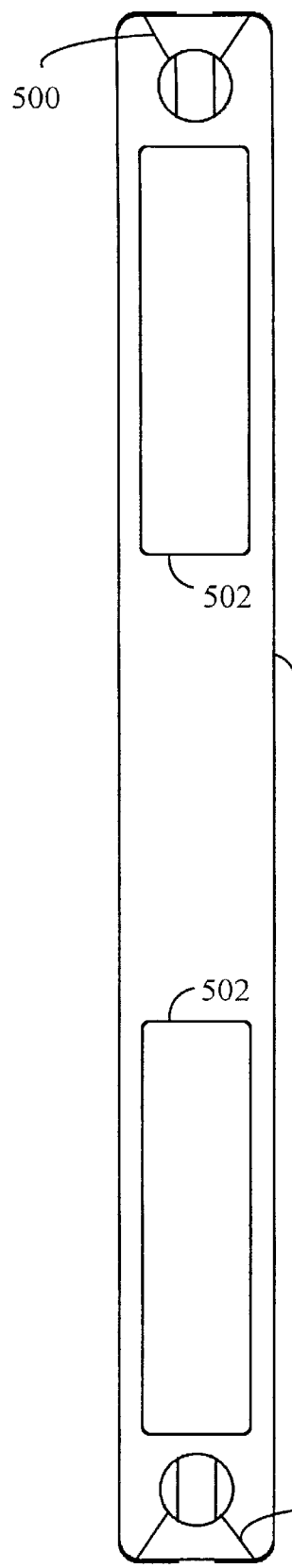
FIGS. 5A and 5B show the transmitter unit when the screen is on the outer surface of the transmitter unit and in contact with skin.
Figure 5B:
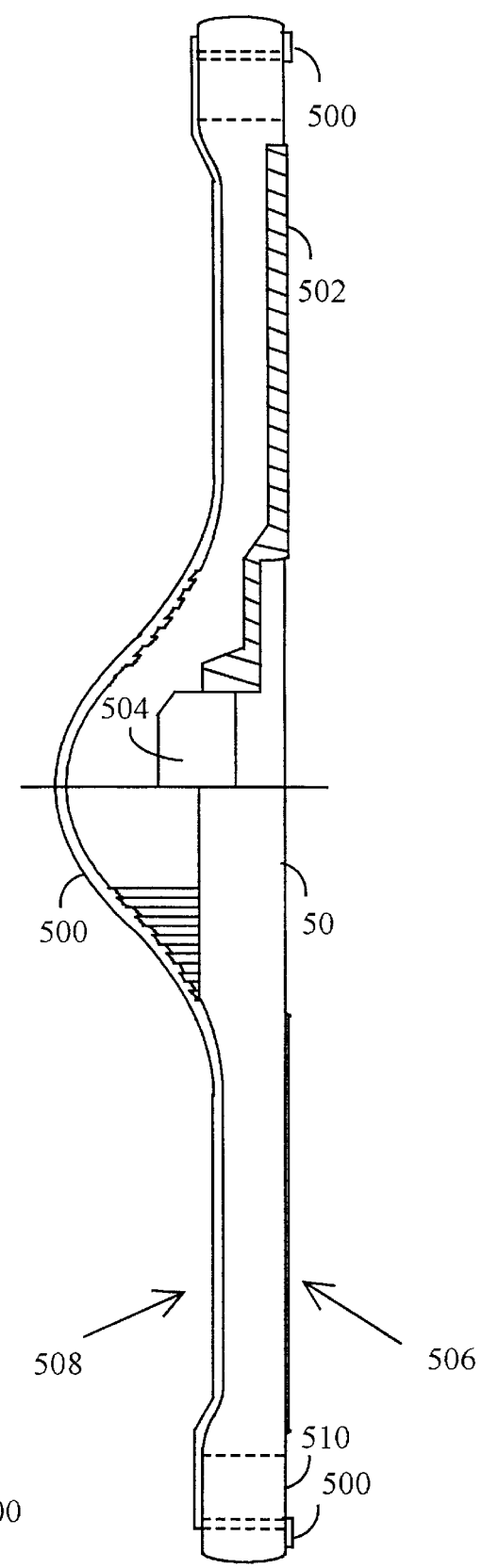

FIGS. 5A and 5B show an example of the inventive solution, wherein a screen 500 is electrically coupled to skin. Electrodes 502 are attached to a belt-like supporting structure 50. Hence, the screen 500 substantially entirely covers a surface 508 without skin contact and continuously extends to a surface 506 with skin contact through an opening 510 in the belt-like supporting structure 50. The point of the skin contact and the coverage of the screen 500 are not, however, highly relevant for the invention but they can be implemented in various ways.

Figure 6:
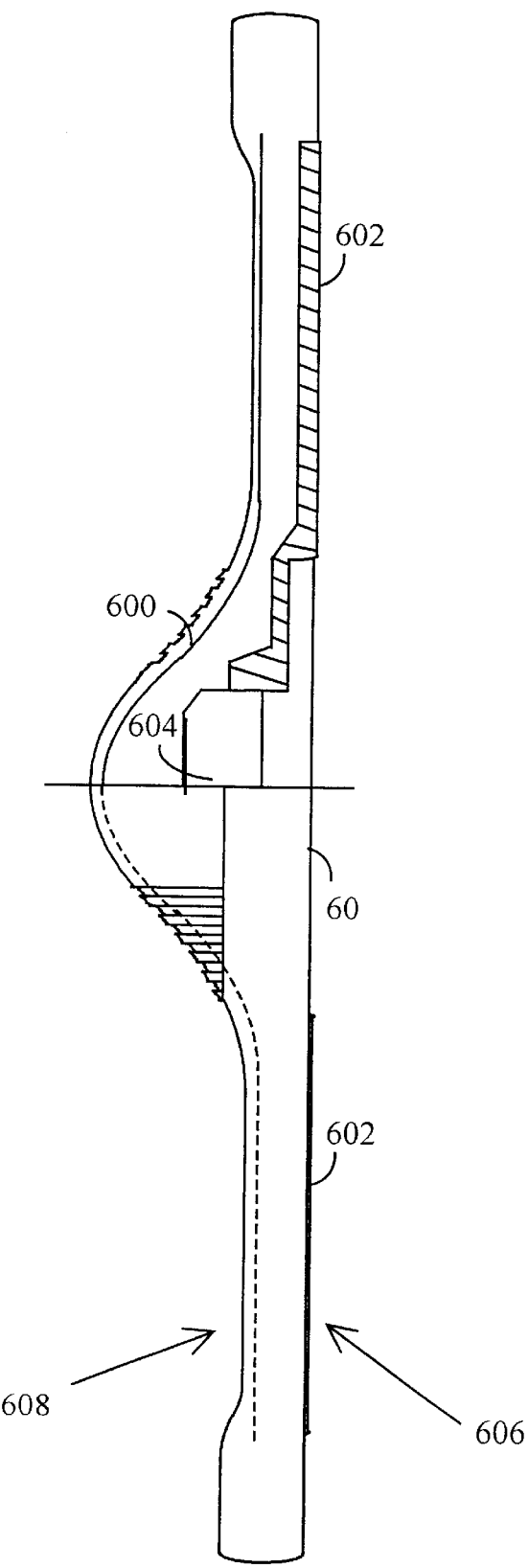
FIG. 6 shows the transmitter unit with the screen located inside the coating material.

FIG. 6 shows an inventive solution wherein a screen 600 is located inside the material of a supporting structure 60 serving as the encasement. Naturally, the screen 600 is however located between an upper surface 608 without skin contact and an electrical circuit 604. Furthermore, the screen 600 can come into contact with skin on a surface 606 with skin contact, as in the solutions of FIGS. 5A and 5B, although skin contact is not necessary for the inventive solution.

Figure 7:
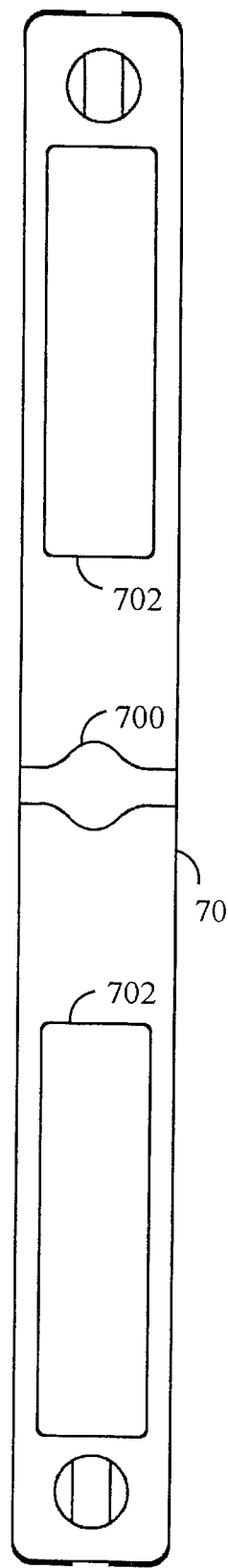
FIG. 7 shows the transmitter unit with the screen coming into contact with skin between the electrodes.

FIG. 7 shows still another embodiment of skin contact in accordance with the inventive solution. The skin contact of a screen 700 on the surface of a supporting structure 70 is located between electrodes 702 on the skin contact surface. The size of the skin contact of the screen 700 is restricted by the fact that the screen must not short-circuit the skin contact zone between the electrodes 702.

Figure 8A:
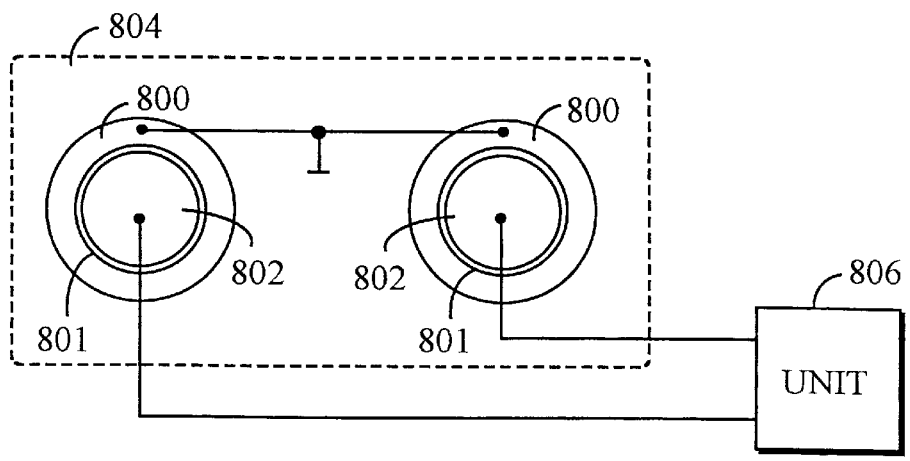
FIG. 8A shows a protecting structure around the electrodes.
Figure 8B:
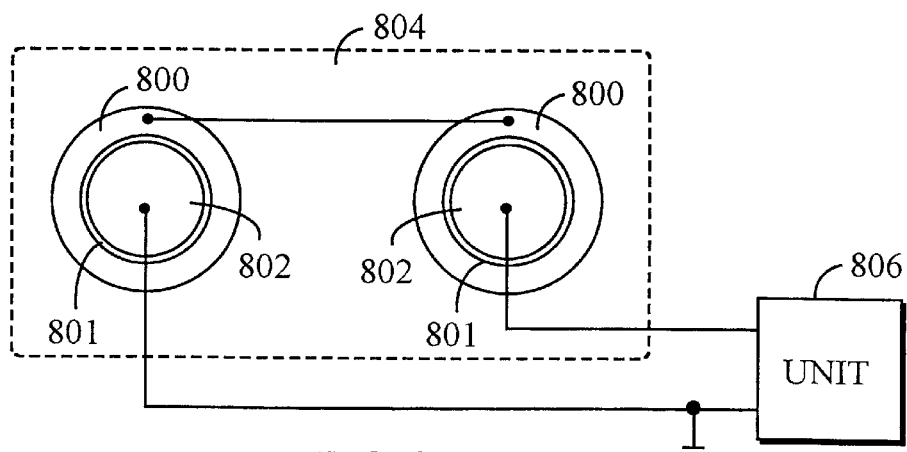
FIG. 8B shows the protecting structure around the electrodes.
Figure 8C:
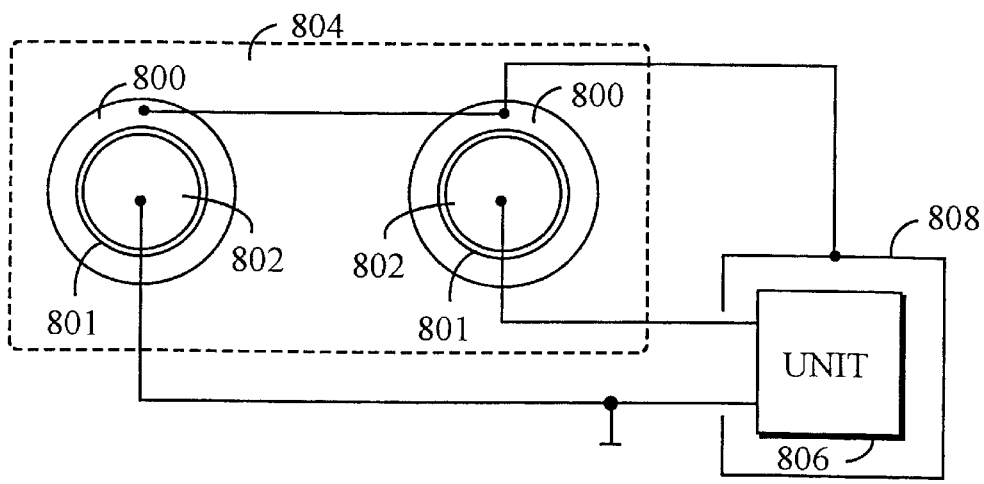
FIG. 8C shows the protecting structure around the electrodes.

In capacity coupling, the electric field between electrodes and skin, in other words the affected zone associated with the electrodes, extends beyond the actual electrode zone, which causes changes that occur on the edge of the electrodes to affect a signal to be measured. Such interference is generated for example when the belt-like functional unit moves up and down during exercise such as jumping. FIG. 8A shows an inventive solution wherein electrodes 802 are enveloped with a protecting structure 800 which belongs to the inventive screen (in FIGS. 1 to 7 the screen 100, 200, 300, 400, 500, 600, 700), the protecting structure reducing interference generated in connection with jumping, for example. The protecting structures of the electrodes 802 are electrically coupled to each other and earthed for instance to the protective earth of the functional unit. It is usually preferable to separate the protecting structure 800 from the electrode 802 by an isolating material layer 801, marked with a bold line. During use, the electrodes 802 come into contact with skin 804. The protecting structure 800 is also coupled to the skin, the protecting structure 800 thus forming a joint potential with the skin 804. The signals of the electrodes 802 propagate to an electrical circuit 806 of the functional unit. FIG. 8B presents a similar solution to the one in FIG. 8A, with the exception that instead of the protecting structure 800, the earthing has been performed to the other input pole of the electrical circuit 806. Also in FIG. 8C earthing has been performed to the input pole of the electrical circuit 806. Furthermore, the protecting structure 800 is electrically coupled to a unique screen 808 of the electrical circuit 806. The protecting structure 800 can also be electrically coupled to the screen 100, 200, 300, 400, 500, 600, 700 shown in FIGS. 1 to 7 (not shown in FIGS. 8A to 10).

Figure 9:
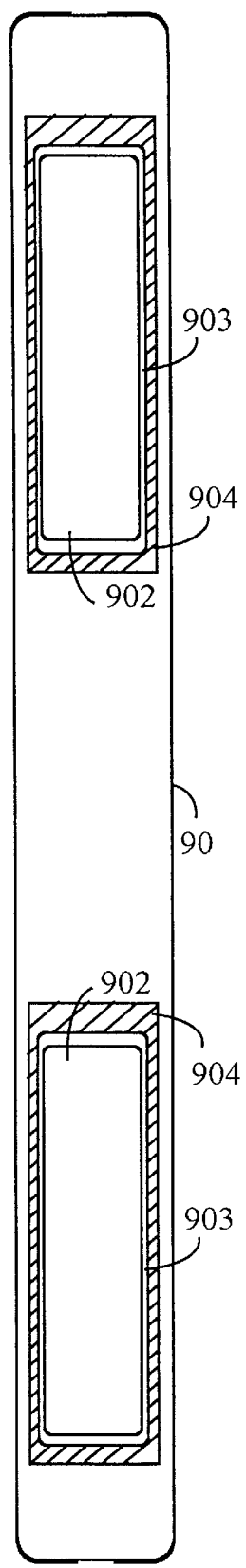
FIG. 9 shows the protecting structure in the transmitter's belt-like supporting structure.
Figure 10:
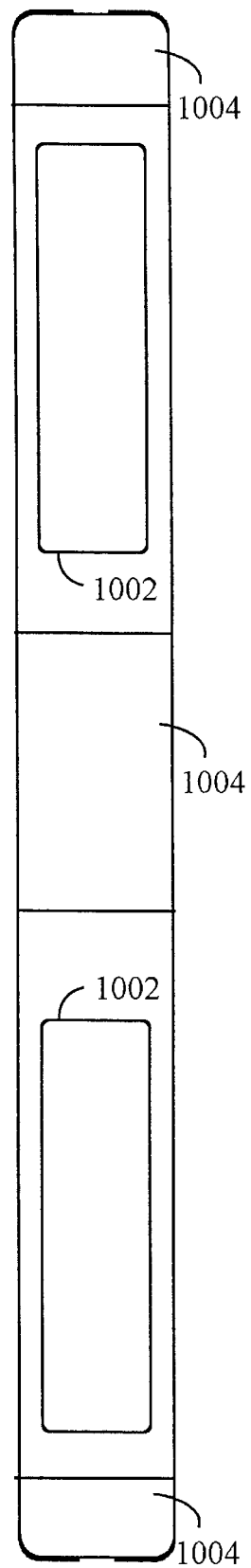
FIG. 10 shows the protecting structure in the transmitter's belt-like supporting structure.

FIG. 9 shows how a protecting structure 904 is positioned around an electrode 902 when the functional unit is for instance a belt-like transmitter unit to be attached around the chest. In the present solution, the protecting structure 904 winds around the electrode 902 and the protecting structure 904 is also in this case preferably electrically separated from the electrode 902 by an isolating material layer 903, marked with a bold line. In FIG. 10, a protecting structure 1004 is a separate zone in the vicinity of electrodes 1002. The protecting structure 1004 can extend to the side without skin contact of the supporting structure of the belt-like functional unit.

Figures 11A, 11B:
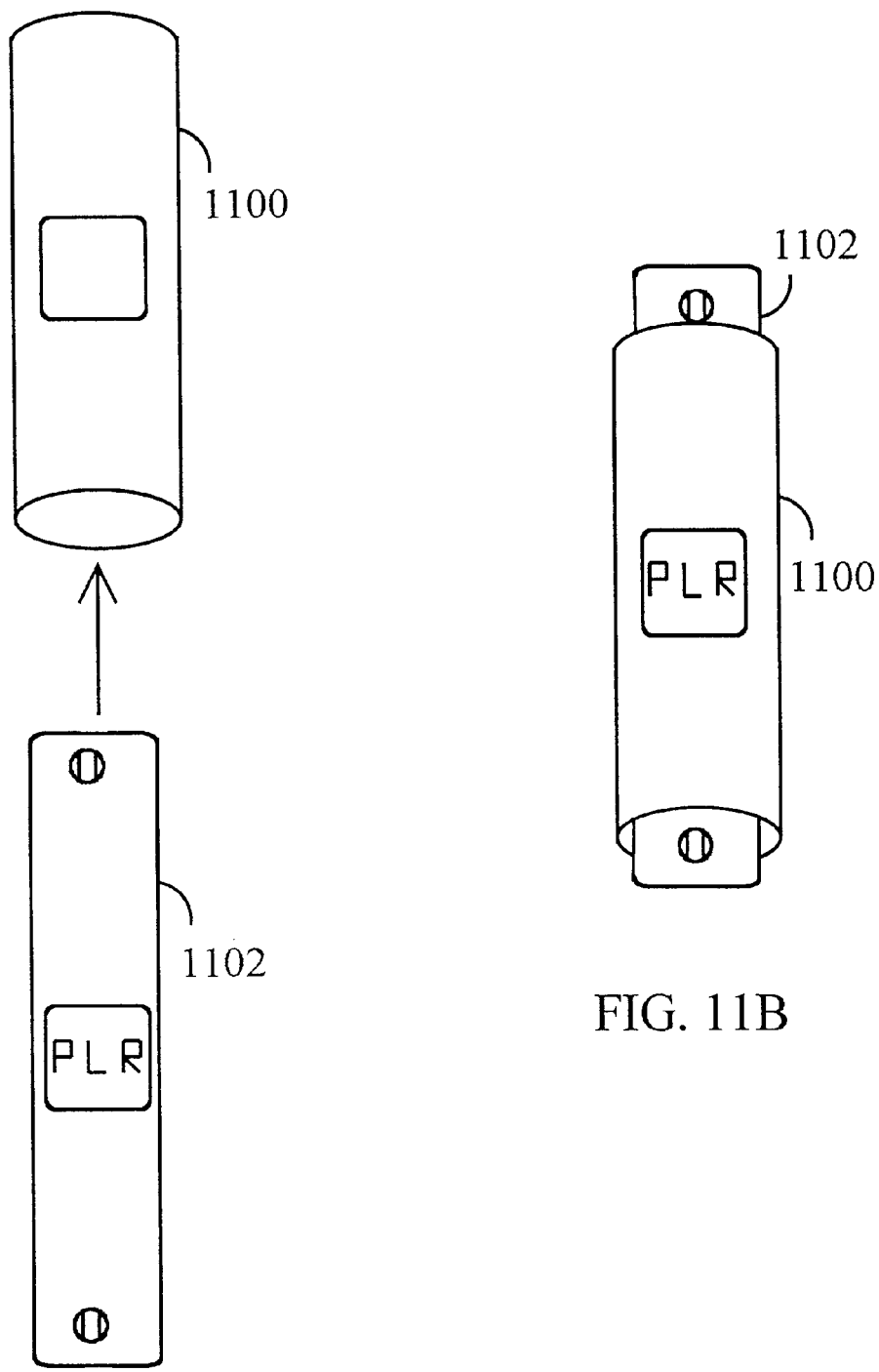
FIG. 11A shows a functional unit and the screen separately.
FIG. 11B shows the functional unit inside the screen.

In the solution of the invention, the screen can also be a completely attachable, detachable and separate structure in relation to the functional unit. In such a case, the screen can be placed on the functional unit, if desired. FIG. 11A shows one example of a detachable and attachable screen, which can be implemented in various ways. In FIG. 11A, a functional unit 1102 and a screen 1100 are separate. The screen 1100 has openings for electrodes. The functional unit 1102 can for example be inserted in the screen 1100 or placed on the belt structure. FIG. 11B shows a situation wherein the functional unit 1102 is inserted in the screen 1100.

The screen of the invention, intended particularly for protecting the electrodes, can be made of conductive polymer, metal or conductive compound plastic comprising electrically non-conductive plastic and electrically conductive material. The screen can be a separate sheet or a layer on or in the coating material of the functional unit. The coating material itself can also be conductive, in which case the conductivity should be sufficiently low in order not to disturb the operation of the electrical circuit by decreasing the signal to be measured. If a sheet-like screen is used, the sheet resistance of the sheet should be sufficiently low in order to accomplish the protecting effect, but sufficiently high for the signal not to decrease due to short circuit when the protection is coupled from two or more points in the vicinity of the electrodes.

Although the invention is described above with reference to the examples in accordance with the accompanying drawings, it is obvious that the invention is not restricted thereto but the invention can be modified in many ways within the scope of the inventive idea disclosed in the attached claims.

What is claimed is:

1. An assembly comprising:

a non-invasive functional unit for measuring the function of at least one organ through skin contact, the functional unit including a supporting structure, an electrical circuit, and electrodes for contacting the skin, the electrodes being operatively coupled to the electrical circuit and mechanically coupled to the supporting structure, and a first screen arranged to closely follow the electrodes or the supporting structure at least at the electrodes, the first screen being made of an electrically conductive material, the first screen being positioned such that when the electrodes contact the skin, the electrodes are substantially located between the first screen and the skin, and a second screen coupled to the first screen for protecting the electrical circuit, wherein the non-invasive functional unit is a belt-like transmitter unit adapted to be worn against the skin, and wherein the second screen is electrically coupled to the first screen.

2. An assembly as described in claim 1, wherein said first screen is positioned on the outer surface of the supporting structure.

3. An assembly as described in claim 1, wherein the first screen is positioned for protecting only the electrodes.

4. An assembly as described in claim 1, wherein the first screen is constructed for protecting the electrodes from static electricity.

* * * * *